United States Patent
Wu et al.

(10) Patent No.: US 9,238,620 B1
(45) Date of Patent: Jan. 19, 2016

(54) PHARMACEUTICAL USES OF SULFUR-CONTAINING COMPOUND

(71) Applicant: NATIONAL SUN YAT-SEN UNIVERSITY, Kaohsiung (TW)

(72) Inventors: Chieh-Hsi Wu, Kaohsiung (TW); Jyh-Horng Sheu, Kaohsiung (TW); Chih-Yi Chen, Kaohsiung (TW); Yi-Chung Chien, Kaohsiung (TW); Shuo-Chueh Chen, Kaohsiung (TW); Chun-Hsu Pan, Kaohsiung (TW); Chiung-Yao Huang, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 0 days.

(21) Appl. No.: 14/327,482

(22) Filed: Jul. 9, 2014

(51) Int. Cl.
| | |
|---|---|
| C07C 317/24 | (2006.01) |
| C07C 323/52 | (2006.01) |
| C07C 323/41 | (2006.01) |
| C07D 295/185 | (2006.01) |
| C07C 323/22 | (2006.01) |
| C07C 317/44 | (2006.01) |
| C07C 317/28 | (2006.01) |

(52) U.S. Cl.
CPC ............. C07C 317/24 (2013.01); C07C 317/28 (2013.01); C07C 317/44 (2013.01); C07C 323/22 (2013.01); C07C 323/41 (2013.01); C07C 323/52 (2013.01); C07D 295/185 (2013.01)

(58) Field of Classification Search
CPC .................................................... C07C 317/24
USPC ......................................................... 514/237
See application file for complete search history.

(56) References Cited

U.S. PATENT DOCUMENTS

| 2005/0267075 A1 | 12/2005 | Allen et al. |
| 2013/0172355 A1 | 7/2013 | Sheu et al. |

FOREIGN PATENT DOCUMENTS

| JP | 2002-121182 | 4/2002 |
| TW | 200909401 | 3/2009 |

OTHER PUBLICATIONS

Saba, N.F. et. al., Chemoprevention strategies for patients with lung cancer in the context of screening. Clin. Lung Cancer 2005, 7, 92-99.
Li, C.M. et. al., 2-Arylthiazolidine-4-carboxylic acid amides (ATCAA) target dual pathways in cancer cells: 5'-AMP-activated protein kinase (AMPK)/mTOR and PI3K/Akt/mTOR pathways. Int. J. Oncol. 2010, 37, 1023-1030.
Man, S. et. al., Formosanin C-inhibited pulmonary metastasis through repression of matrix metalloproteinases on mouse lung adenocarcinoma. Cancer Biol. Ther. 2011, 11, 592-598.
Lirdprapamongkol, K. et. al., Vanillin suppresses metastatic potential of human cancer cells through PI3K inhibition and decreases angiogenesis in vivo. J. Agric. Food Chem. 2009, 57, 3055-3063.
Kodate, M. et. al., Expression of matrix metalloproteinase (gelatinase) in T1 adenocarcinoma of the lung. Pathol. Int. 1997, 47, 461-469.
Weng, C.J. et. al., Evaluation of anti-invasion effect of resveratrol and related methoxy analogues on human hepatocarcinoma cells. J. Agric. Food Chem. 2010, 58, 2886-2894.
Campbell, I.G. et. al., Mutation of the PIK3CA gene in ovarian and breast cancer. Cancer Res. 2004, 64, 7678-7681.
Gupta, A.K. et. al., Signaling pathways in NSCLC as a predictor of outcome and response to therapy. Lung 2004, 182, 151-162.
Shih, Y.W. et. al., Alpha-chaconine-reduced metastasis involves a PI3K/Akt signaling pathway with downregulation of NF-kappaB in human lung adenocarcinoma A549 cells. J. Agric. Food Chem. 2007, 55, 11035-11043.
Jean, Y.H. et. al., Inducible nitric oxide synthase and cyclooxygenase-2 participate in anti-inflammatory and analgesic effects of the natural marine compound lemnalol from Formosan soft coral Lemnalia cervicorni. Eur. J. Pharmacol. 2008, 578, 323-331.
Jean, Y.H. et. al., Capnellene, a natural marine compound derived from soft coral, attenuates chronic constriction injury-induced neuropathic pain in rats. Br. J. Pharmacol. 2009, 158, 713-725.
Tseng, Y.J. et. al., Nanolobatolide, a new C18 metabolite from the Formosan soft coral Sinularia nanolobata. Org. Lett. 2009, 11, 5030-5032.
Chao, C.H. et. al., Cytotoxic and anti-inflammatory cembranoids from the soft coral Lobophytum crassum. J. Nat. Prod. 2008, 71, 1819-1824.
Wen, Z.H. et. al., A neuroprotective sulfone of marine origin and the in vivo anti-inflammatory activity of an analogue. Eur. J. Med. Chem. 2010, 45, 5998-6004.
Lai, K.C. et. al., Benzyl isothiocyanate (BITC) inhibits migration and invasion of human colon cancer HT29 cells by inhibiting matrix metalloproteinase-2 1-9 and urokinase plasminogen (uPA) through PKC and MAPK signaling pathway. J. Agric. Food Chem. 2010, 58, 2935-2942.
Chan, K.C. et. al., Mulberry leaf extract inhibits vascular smooth muscle cell migration involving a block of small GTPase and Akt/NF-kappaB signals. J. Agric. Food Chem. 2009, 57, 9147-9153.
Zeng, Z.Z. et. al., Role of focal adhesion kinase and phosphatidylinositol 3'-kinase in integrin fibronectin receptor-mediated, matrix metalloproteinase-1-dependent invasion by metastatic prostate cancer cells. Cancer Res. 2006, 66, 8091-8099.
Choi, Y.A. et. al., Group IB secretory phospholipase A2 promotes matrix metalloproteinase-2-mediated cell migration via the phosphatidylinositol 3-kinase and Akt pathway. J. Biol. Chem. 2004, 279, 36579-36585.
Chen, Y.Y. et. al., Ethanol extracts of fruiting bodies of Antrodia cinnamomea exhibit anti-migration action in human adenocarcinoma CL1-0 cells through the MAPK and PI3K/AKT signaling pathways. Phytomedicine 2012, 19, 768-778.

(Continued)

*Primary Examiner* — Taofiq A Solola
(74) *Attorney, Agent, or Firm* — WPAT, P.C.; Anthony King

(57) ABSTRACT

The invention relates to uses of the sulfur-containing compound in inhibiting activities of a factor related to cancer metastasis and/or growth. Preferably, the invention relates to uses of the sulfur-containing compound in inhibiting lung cancer metastasis and/or growth.

4 Claims, 8 Drawing Sheets

(56) References Cited

OTHER PUBLICATIONS

Shuo-Chueh Chen et. al., Inhibitory Effect of Dihydroaustrasulfone Alcohol on the Migration of Human Non-Small Cell Lung Carcinoma A549 Cells and the Antitumor Effect on a Lewis Lung Carcinoma-Bearing Tumor Model in C57BL AJ Mice. Marine Drugs 2014, 12, 196-213.

Shuo-Chueh Chen et. al., Role of Vascular Endothelial Growth Factor C in Resected Stage I Lung Cancer and New Drugs Investigation for Anti-migration of Lung Cancer Cell. Institute of Clinical Medicine, China Medical University doctoral dissertation, 2014 (Jan. 1, 2014).

Office action and Search Report issued on Nov. 11, 2015 for the corresponding Taiwan Patent Application No. 103122736.

English translation of the Search Report issued on Nov. 11, 2015 for the corresponding Taiwan Patent Application No. 103122736.

TW 200909401 A corresponds to US2013172355 A1. published Jul. 4, 2013.

English abstract translation of JP 2002-121182. published Apr. 23, 2002.

PHARMACEUTICAL USES OF SULFUR-CONTAINING COMPOUND

BACKGROUND OF THE INVENTION

1. Field of the Invention

The invention relates to uses of a sulfur-containing compound. Said sulfur-containing compound has ability to inhibit activities of a factor related to cancer metastasis and/or growth and to inhibit lung cancer metastasis and/or growth.

2. Description of the Related Art

Non-small cell lung cancer (NSCLC) is one of the main causes of cancer death, and its incidence is increasing. Surgery, radiotherapy, and chemotherapy are the major treatment methods to reduce lung cancer mortality (Saba, N. F.; Khuri, F. R. Chemoprevention strategies for patients with lung cancer in the context of screening. *Clin. Lung Cancer* 2005, 7, 92-99), however, these treatments have harmful side effects on normal healthy cells in the human body. Therefore, it is important to discover new agents to treat lung cancer safely without affecting the body's healthy cells. The deregulation of signaling pathways such as PI3K/Akt is often implicated in the pathogenesis of NSCLC (Li, C. M.; Narayanan, R.; Lu, Y.; Hurh, E.; Coss, C. C.; Barrett, C. M.; Miller, D. D.; Dalton, J. T. 2-Arylthiazolidine-4-carboxylic acid amides (ATCAA) target dual pathways in cancer cells: 5'-AMP-activated protein kinase (AMPK)/mTOR and PI3K/Akt/mTOR pathways. *Int. J. Oncol.* 2010, 37, 1023-1030). Thus, the need for the accelerated development of effective NSCLC therapies is critical. At present, the design of new therapeutic strategies targeting multiple signaling pathways for more effective disease management in NSCLC is a primary focus of current research.

Overgrowth, invasion, and metastasis are the major characteristics of malignancy with poor clinical outcome. Malignant tumor progression depends upon the capacity to invade, metastasize, and promote the angiogenic host response. The dynamics of extracellular matrix (ECM) remodeling have been the focus of intense investigation for many years. The degradative process is mainly mediated by matrix metalloproteinases (MMPs), which are a family of at least 20 zinc-dependent endopeptidases best known for their ability to hydrolyze ECM components (Man, S.; Gao, W.; Zhang, Y.; Liu, Z.; Yan, L.; Huang, L.; Liu, C. Formosanin C-inhibited pulmonary metastasis through repression of matrix metalloproteinases on mouse lung adenocarcinoma. *Cancer Biol. Ther.* 2011, 11, 592-598). MMP-9 is expressed in large quantities in the human lung cancer cell line A549 and might play an important role in tumor invasion (Lirdprapamongkol, K.; Kramb, J. P.; Suthiphongchai, T.; Surarit, R.; Srisomsap, C.; Dannhardt, G.; Svasti, J. Vanillin suppresses metastatic potential of human cancer cells through PI3K inhibition and decreases angiogenesis in vivo. *J. Agric. Food Chem.* 2009, 57, 3055-3063). The activity of MMPs is prone to inhibition by endogenous tissue inhibitor of metalloproteinases (TIMPs), which are specific inhibitors of MMPs, and the imbalance between MMPs and TIMPs may contribute to the degradation or deposition of the ECM (Kodate, M.; Kasai, T.; Hashimoto, H.; Yasumoto, K.; Iwata, Y.; Manabe, H. Expression of matrix metalloproteinase (gelatinase) in T1 adenocarcinoma of the lung. *Pathol. Int.* 1997, 47, 461-469). Mitogen-activated protein kinases (MAPKs) play an important regulatory role in cell growth, differentiation, apoptosis, and metastasis (Weng, C. J.; Wu, C. F.; Huang, H. W.; Wu, C. H.; Ho, C. T.; Yen, G. C. Evaluation of anti-invasion effect of resveratrol and related methoxy analogues on human hepatocarcinoma cells. *J. Agric. Food Chem.* 2010, 58, 2886-2894). In addition, the phosphatidylinositol-3-kinase/serine/threonine protein kinase (or protein kinaseB)(PI3K/Akt) signal transduction pathway is involved in the development, progression, and metastasis of various tumors (Campbell, I. G.; Russell, S. E.; Choong, D. Y.; Montgomery, K. G.; Ciavarella, M. L.; Hooi, C. S.; Cristiano, B. E.; Pearson, R. B.; Phillips, W. A. Mutation of the PIK3CA gene in ovarian and breast cancer. *Cancer Res.* 2004, 64, 7678-7681) (Gupta, A. K.; Soto, D. E.; Feldman, M. D.; Goldsmith, J. D.; Mick, R.; Hahn, S. M.; Machtay, M.; Muschel, R. J.; McKenna, W. G. Signaling pathways in NSCLC as a predictor of outcome and response to therapy. *Lung* 2004, 182, 151-162) (Shih, Y. W.; Chen, P. S.; Wu, C. H.; Jeng, Y. F.; Wang, C. J. Alpha-chaconine-reduced metastasis involves a PI3K/Akt signaling pathway with downregulation of NF-kappaB in human lung adenocarcinoma A549 cells. *J. Agric. Food Chem.* 2007, 55, 11035-11043).

Taiwan is an island and so us surrounded by the sea. In recent studies, the majority of natural marine products have promising biological activities. Jean et al. (Jean, Y. H.; Chen, W. F.; Duh, C. Y.; Huang, S. Y.; Hsu, C. H.; Lin, C. S.; Sung, C. S.; Chen, I. M.; Wen, Z. H. Inducible nitric oxide synthase and cyclooxygenase-2 participate in anti-inflammatory and analgesic effects of the natural marine compound lemnalol from Formosan soft coral *Lemnalia cervicorni*. *Eur. J. Pharmacol.* 2008, 578, 323-331) (Jean, Y. H.; Chen, W. F.; Sung, C. S.; Duh, C. Y.; Huang, S. Y.; Lin, C. S.; Tai, M. H.; Tzeng, S. F.; Wen, Z. H. Capnellene, a natural marine compound derived from soft coral, attenuates chronic constriction injury-induced neuropathic pain in rats. *Br. J. Pharmacol.* 2009, 158, 713-725) showed that natural products isolated from Taiwanese soft corals, such as lemnalol and capnellene, are useful for the treatment of inflammatory diseases in rats. In some studies, the investigation of bioactive marine natural products has led to the isolation of compounds with neuroprotective (Tseng, Y. J.; Wen, Z. H.; Dai, C. F.; Chiang, M. Y.; Sheu, J. H. Nanolobatolide, a new C18 metabolite from the Formosan soft coral *Sinularia nanolobata*. *Org. Lett.* 2009, 11, 5030-5032) and anti-inflammatory (Chao, C. H.; Wen, Z. H.; Wu, Y. C.; Yeh, H. C.; Sheu, J. H. Cytotoxic and anti-inflammatory cembranoids from the soft coral *Lobophytum crassum*. *J. Nat. Prod.* 2008, 71, 1819-1824) activities from soft corals. In previous studies, dihydroaustrasulfone alcohol produced in vitro anti-inflammatory activity. Wen et al. (Wen, Z. H.; Chao, C. H.; Wu, M. H.; Sheu, J. H. A neuroprotective sulfone of marine origin and the in vivo anti-inflammatory activity of an analogue. *Eur. J. Med. Chem.* 2010, 45, 5998-6004) showed that dihydroaustrasulfone alcohol not only exhibited in vitro anti-inflammatory activity but also showed potent therapeutic ability in the treatment of neuropathic pain, atherosclerosis, and multiple sclerosis in rats.

SUMMARY OF THE INVENTION

In the present invention, the anti-metastatic effects and/or anti-tumot growth activity and underlying mechanisms of a sulfur-containing compound are provided.

One object of the invention is to provide uses of a sulfur-containing compound. Said sulfur-containing compound can be chemically synthesized and can significantly inhibit the functions of inflammatory proteins in vitro. Furthermore, the sulfur-containing compound is shown to be able to inhibit activities of a factor related to cancer metastasis and/or growth and to inhibit lung cancer metastasis and/or growth.

DETAILED DESCRIPTION OF THE INVENTION

Figure 1A:
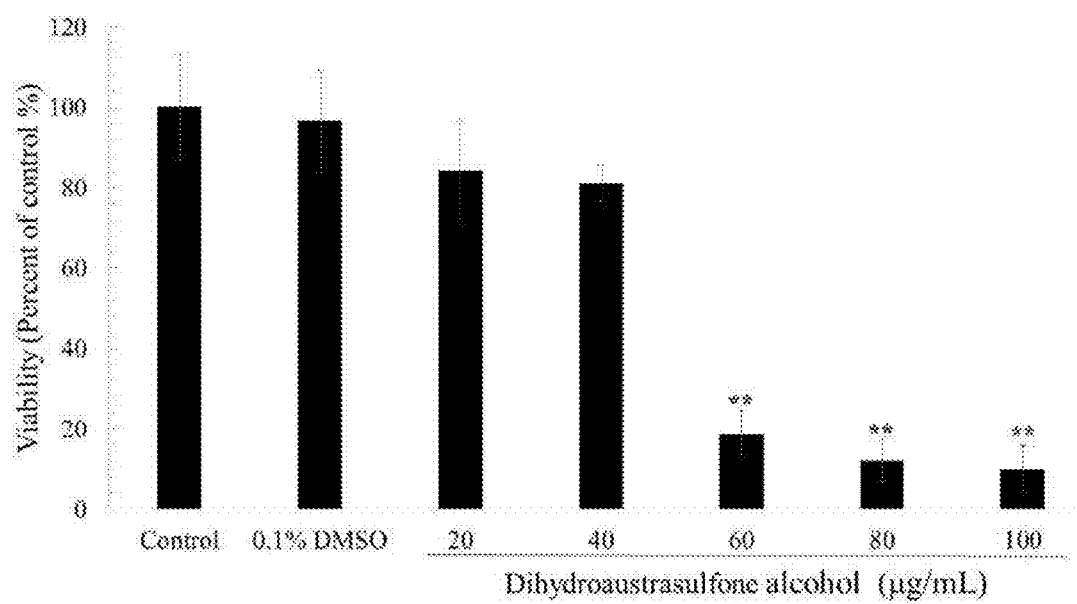
FIG. 1. Cytotoxicity of dihydroaustrasulfone alcohol (formula 3) to A549 cells. (a) Viability of A549 cells incubated with dihydroaustrasulfone alcohol (20, 40, 60, 80 or 100 μg/mL) for 24 h. Cell viability was measured using an MTT assay and is expressed as the % of cell survival relative to the control, which means sample without drug treatment as all of the results. (b) Flow cytometric analysis of the effect of dihydroaustrasulfone alcohol on the cell cycle of A549 cells. The cells were treated with dihydroaustrasulfone alcohol at concentrations of 20, 40, 60 or 80 μg/mL for 24 h. The value on the x-axis represents the DNA content, while the shaded area indicates the percentage of cells at the S phase, blue area indicate sub-G1 phase, and red areas indicate G1 phase (left) and G2 phase (right), individually. This graph shows the percentage of sub-G1 contents in A549 cells treated with dihydroaustrasulfone alcohol. The values are the means of three separate experiments, with the standard deviation represented by vertical bars. *P<0.05; P<0.01; *P<0.001.

The sulfur-containing compound according to the invention is represented by the following general formula 1,

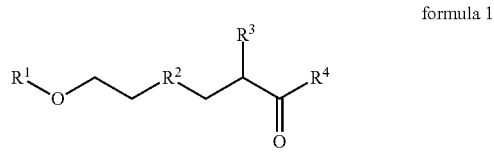

formula 1 wherein:
$R^1$ is selected from the group consisting of H, $R^5$ and $R^5C(=O)$;

$R^2$ is selected from the group consisting of S and $(O=)S(=O)$;

$R^3$ is selected from the group consisting of H, $CH_3$ and $CH_2CH_2C(=O)OR^5$;

$R^4$ is selected from the group consisting of $R^5$, $OR^5$,

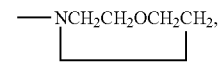

$N(R^5)2$, $NH_2$, $NHR^5$ and OH; and $R^5$ is selected from an alkyl group having one to six carbon atoms and an unsubstituted or substituted phenyl group; and preferably, $R^5$ is selected from the group consisting of methyl, ethyl, and unsubstituted phenyl, provided that when $R^3$ is $CH_2CH_2C(=O)OR^5$, R4 is $OR^5$; and when $R^1$ is H, $R^2$ is S and $R^3$ is H, $R^4$ is not $CH_3$.

According to the preferred embodiments of the invention, the compound represented by general formula 1 is represented by one of the following formulae 3 to 22,

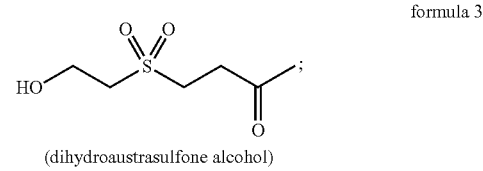

formula 3

(dihydroaustrasulfone alcohol)

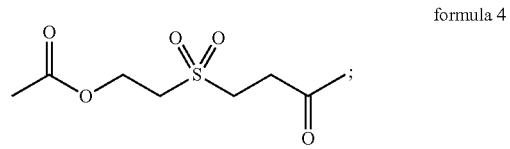

formula 4

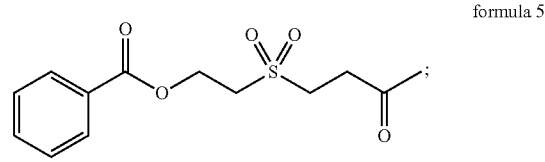

formula 5

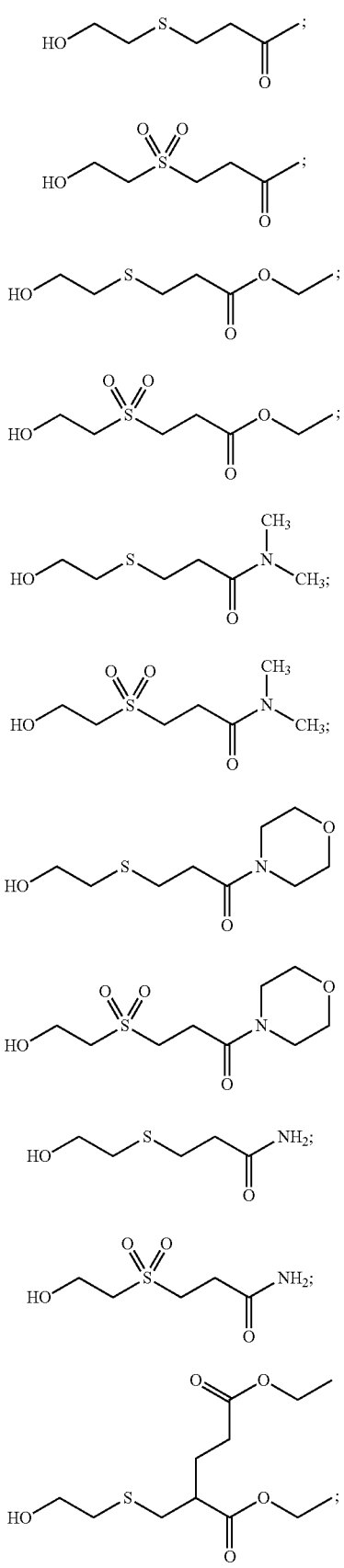
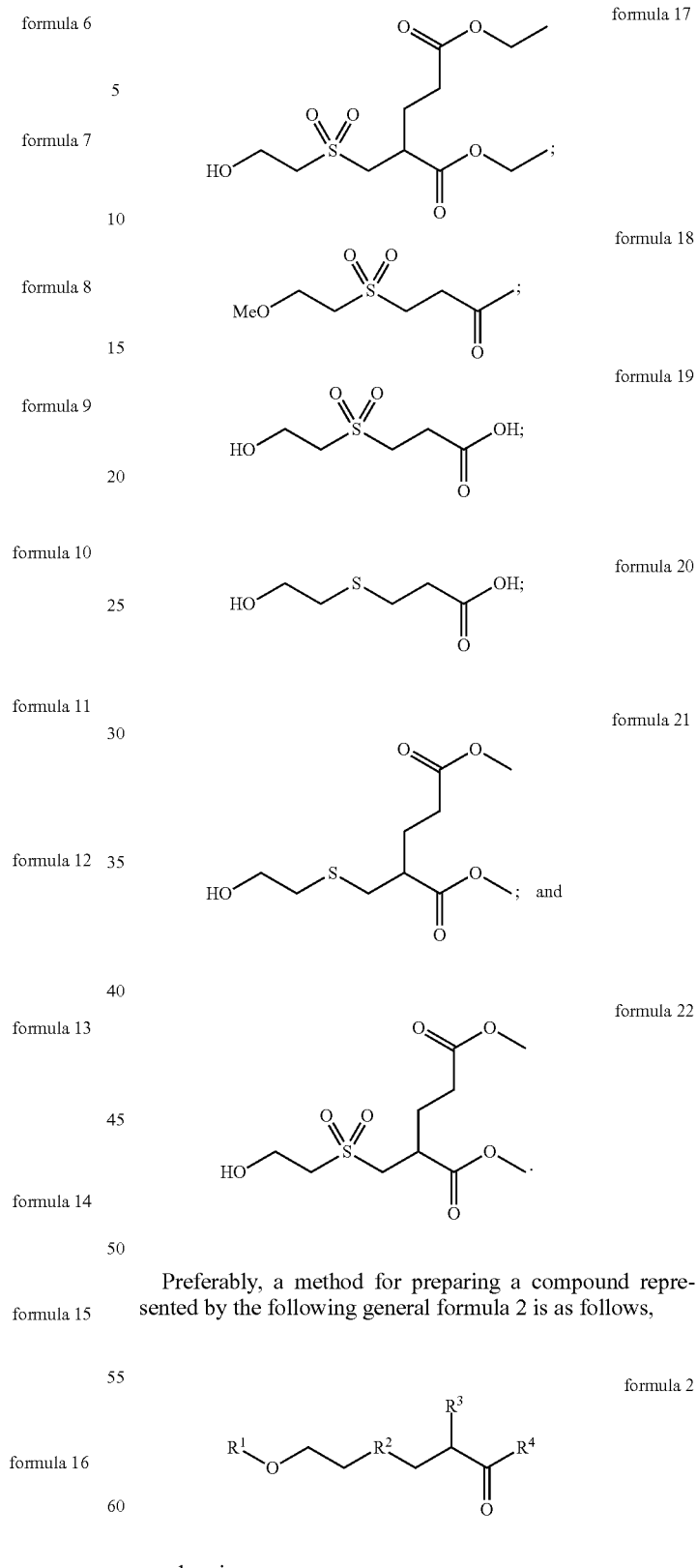
Preferably, a method for preparing a compound represented by the following general formula 2 is as follows,
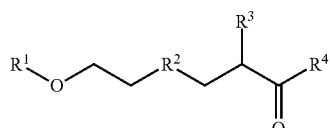
formula 2
wherein:
R¹ is selected from the group consisting of H, R⁵ and R⁵C(═O);
R² is selected from the group consisting of S and (O═)S (═O);

$R^3$ is selected from the group consisting of H, $CH_3$ and $CH_2CH_2C(=O)OR^5$;

R4 is selected from the group consisting of $R^5$, $OR^5$,

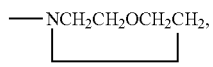

$N(R^5)_2$, $NH_2$, $NHR^5$ and OH; and $R^5$ is selected from an alkyl group having one to six carbon atoms and an unsubstituted or substituted phenyl group; provided that when $R^3$ is $CH_2CH_2C(=O)OR^5$, $R^4$ is $OR^5$, comprising:

(I) when $R^1$ is H and $R^2$ is S, reacting a compound represented by the following general formula 23, formula 23

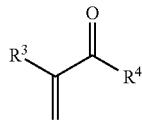

with 2-mercaptoethanol represented by the following formula 24, formula 24

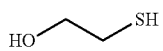

to obtain a compound represented by the following general formula 25 formula 25

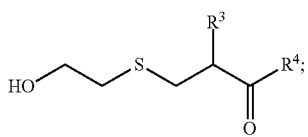

(II) when $R^1$ is $R^5C(=O)$, esterifying the compound represented by general formula 25;
(III) when $R^1$ is $R^5$, alkylating the compound represented by general formula 25;
(IV) when $R^2$ is $(O=)S(=O)$, oxidizing the compound represented by general formula 25;
(V) when $R^1$ is $R^5C(=O)$ and $R^2$ is $(O=)S(=O)$, esterifying and oxidizing the compound represented by general formula 25;
(VI) when $R^1$ is $R^5$ and $R^2$ is $(O=)S(=O)$, alkylating and oxidizing the compound represented by general formula 25; and
(VII) when $R^1$ is H, $R^2$ is S, $R^3$ is H and $R^4$ is $CH_3$, reacting a compound represented by the following formula 27, formula 27

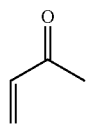

with 2-mercaptoethanol represented by formula 24 in the presence of triethylamine.

Particularly, the method according to the invention is one of the following methods:

(I) When $R^1$ is H and $R^2$ is S, the method of the invention comprises reacting a compound represented by general formula 23 formula 23

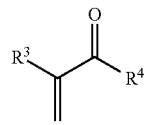

(wherein $R^3$ preferably is H)
with 2-mercaptoethanol represented by formula 24 to obtain the compound represented by general formula 25. Preferably, the above reaction is carried out in the presence of triethylamine. In one embodiment of the invention, the reactants are dissolved in acetone and reacted in ice bath. In another aspect, when $R^3$ is $CH_2CH_2C(=O)OR^5$, the reaction is conducted in the absence of a solvent.

(II) When $R^1$ is $R^5C(=O)$, the method according to the invention comprises esterifying the compound represented by general formula 25. Preferably, the above reaction is carried out in the presence of triethylamine. In one embodiment of the invention, the reactants are dissolved in dichloromethane. In one preferred embodiment of the invention, when $R^1$ is $CH_3C(=O)$, the method comprises reacting the compound represented by general formula 25 with acetic anhydride. In one another preferred embodiment of the invention, when $R^1$ is $C_6H_5C(=O)$, the method comprises reacting the compound represented by general formula 25 with benzoyl chloride.

(III) When $R^1$ is $R^5$, the method according to the invention comprises alkylating the compound represented by general formula 25. In one preferred embodiment of the invention, when $R^1$ is $CH_3$, the method comprises reacting the compound represented by general formula 25 with $CH_3I$.

(IV) When $R^2$ is $(O=)S(=O)$, the method according to the invention comprises oxidizing the compound represented by general formula 25. Preferably, the oxidation is carried out with hydrogen peroxide or m-chloroperoxybenzoic acid. In one embodiment of the invention, when using hydrogen peroxide, the oxidation is catalyzed by $MnSO_4 \cdot H_2O$, and the reactants are dissolved in acetonitrile. When using m-chloroperoxybenzoic acid to carry out the oxidation, the reactants are dissolved in dichloromethane.

(V) When $R^1$ is $R^5C(=O)$ and $R^2$ is $(O=)S(=O)$, the method according to the invention comprises esterifying and oxidizing the compound represented by general formula 25 as mentioned above.

(VI) When $R^1$ is $R^5$ and $R^2$ is $(O=)S(=O)$, the method according to the invention comprises alkylating and oxidizing the compound represented by general formula 25 as mentioned above.

(VII) When $R^1$ is H, $R^2$ is S, $R^3$ is H and $R^4$ is $CH_3$, the method according to the invention comprises reacting a compound represented by formula 27 with 2-mercaptoethanol represented by formula 24 in the presence of triethylamine.

The present invention provides a method for inhibiting activities of a factor related to cancer metastasis and/or growth comprising administering a subject with the compound represented by the general formula 1, wherein the factor related to cancer metastasis and/or growth is selected from the group consisting of matrix metalloproteinase-2, matrix metalloproteinase-9, ERK1/2, p38, JNK 1/2, phosphophatidylinositol-3 kinase, and Akt.

Preferably, the method according to the invention is for inhibiting the activity and expression of matrix metalloproteinase-2, inhibiting the activity and protein expression of matrix metalloproteinase-9, inhibiting the phosphorylation of ERK1/2, inhibiting the phosphorylation of p38, inhibiting the phosphorylation of JNK 1/2, inhibiting the expression of phosphophatidylinositol-3 kinase, and/or inhibiting the phosphorylation of Akt.

The cancer according to the invention is preferably a solid cancer, more preferably, the cancer is lung cancer. In one preferred embodiment of the invention, the lung cancer is non-small cell lung carcinoma. In one another preferred embodiment of the invention, the lung cancer is Lewis lung carcinoma.

The present invention provides a method for inhibiting lung cancer metastasis and/or growth comprising administering a subject with the compound represented by the general formula 1.

The compound represented by general formula 1 can be administered orally or through injection. Preferably, the compound is administered by injection.

In one preferred embodiment of the invention, the compound represented by general formula 1 provides a concentration-dependent inhibitory effect on the migration and motility of human non-small cell lung carcinoma (NSCLC) A549 cells by trans-well and wound healing assays. The results of a zymography assay and Western blot showed that the compound represented by general formula 1 suppressed the activities and protein expression of matrix metalloproteinase-2 and MMP-9. Further investigation revealed that the compound represented by general formula 1 suppressed the phosphorylation of ERK1/2, p38, and JNK1/2. The compound represented by general formula 1 also suppressed the expression of PI3K and the phosphorylation of Akt. Furthermore, the compound represented by general formula 1 markedly inhibited tumor growth in Lewis lung cancer-bearing mice. We concluded that the compound represented by general formula 1 is a compound with anti-migration and anti-tumor growth activity in lung cancer.

The following examples are given for the purpose of illustration only and are not intended to limit the scope of the present invention.

Preparation 1

2-Mercaptoethanol (1.80 g, 98%, 27.14 mmole) and triethylamine (0.53 mL, 3.77 mmole) were added in a round bottom flask containing 22 mL of acetone. Followed by stirring in a 0° C. ice bath, a solution of methyl vinyl ketone (2.31 mL, 27.14 mmole) in 4 mL acetone was dropped into the flask slowly. After the addition, the temperature of the reaction was raised to room temperature, and the reaction was continued for 16 hours. The solvent-free product was subject to silica gel column chromatography to afford a thioether compound represented by the following formula 26 (3.35 g, yield 100%),

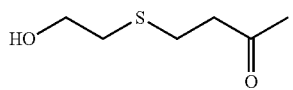

formula 26

Thioether compound represented by formula 26: colorless oil, IR (KBr) $\nu_{max}$ 3405, 1713, 1416, 1362, 1161, 1045, 1010 cm$^{-1}$; $^1$H NMR (CDCl$_3$, 300 MHz) $\delta_H$ 3.73 (2H, dt, J=5.6, 5.4 Hz), 2.75 (4H, br s), 2.72 (2H, t, J=5.4 Hz), 2.46 (1H, t, J=5.6 Hz, OH) 2.17 (3H, s); $^{13}$C NMR (CDCl$_3$, 75 MHz) $\delta_C$ 207.0 (qC), 60.6 (CH$_2$), 43.7 (CH$_2$), 35.6 (CH$_2$), 30.2 (CH$_3$), 25.4 (CH$_2$); ESIMS m/z 171 [M+Na]$^+$; HRESIMS m/z 171.0458 [M+Na]$^+$ (calculated for C$_6$H$_{12}$O$_2$SNa, 171.0456).

Preparation 2

The thioether compound represented by formula 26 (1.00 g, 6.76 mmole) prepared as Preparation 1 and MnSO4.H2O (23 mg, 0.14 mmole) were mixed with acetonitrile (156 mL) in a 500 mL round bottom flask (Flask A) and the mixture was stirred vigorously at room temperature. The aqueous solutions of sodium hydrogen carbonate buffer (115 mL, 0.2 M, pH=8.0) and 30% hydrogen peroxide solution (3.38 mL) were charged into a 250 mL flask at 0° C. and stirred well, and then added slowly into Flask A. After reacting for 2 hours, ethyl acetate/isopropyl alcohol (3:1) was added for extraction (200 mL×6). The combined organic extract was concentrated under reduced pressure and the residue was purified over a silica gel column (eluted with hexane/EtOAc=1:3) for obtaining the compound represented by formula 3 (1.03 g, yield 84%).

Compound represented by formula 3: colorless crystals, mp 59-60° C.; IR (KBr) $\nu_{max}$ 3416, 1715, 1416, 1366, 1311, 1120, 1009 cm$^{-1}$; $^1$H NMR (CDCl$_3$, 300 MHz) $\delta_H$ 4.02 (2H, t, J=5.4 Hz), 3.36 (2H, t, J=7.3 Hz), 3.21 (2H, t, J=5.4 Hz), 2.97 (2H, t, J=7.3 Hz), 2.20 (3H, s); $^{13}$C NMR (CDCl$_3$, 75 MHz) $\delta_C$ 204.9 (qC), 56.0 (CH$_2$), 55.7 (CH$_2$), 48.7 (CH$_2$), 34.9 (CH$_2$), 29.7 (CH$_3$); ESIMS m/z 203 [M+Na]$^+$; HRESIMS m/z 203.0354 [M+Na]$^+$ (calculated for C$_6$H$_{12}$O$_4$SNa, 203.0354).

Preparation 3

To a stirring solution of the thioether compound represented by formula 26 (1.00 g, 6.76 mmole) prepared as Preparation 1 in dichloromethane (64 mL) in a 125 mL round bottom flask was slowly added m-chloroperoxybenzoic acid (2.92 g, 16.90 mmole) in batches. After the addition, the reaction was monitored with TLC until the thioether compound was completely consumed. Then, dichloromethane was removed, and the resulted mixture was added with 100 mL of saturated sodium hydrogen carbonate solution and stirred vigorously. The resulted crude product was extracted with ethyl acetate (100 mL×10) and the combined extract was concentrated under reduced pressure. The obtained product was purified with a silica gel column (eluted with hexane/EtOAc=1:3) to afford the compound represented by formula 3 (1.00 g, yield 82%).

Preparation 4

To a stirring solution of the compound represented by formula 3 (20.0 mg, 0.114 mmole) and triethylamine (25 µL) in dichloromethane (2 mL) was slowly added acetic anhydride (40 µL) at room temperature. The reaction was continued for 16 hours and the solvent-free product was subjected to silica gel column chromatography (eluted with hexane/EtOAc=2:3) for obtaining a compound represented by formula 4 (25.0 mg, yield 98%).

Compound represented by formula 4: colorless oil, IR (KBr) $\nu_{max}$ 1743, 1720, 1366, 1317, 1234, 1125, 1070, 1036 cm$^{-1}$; $^1$H NMR (CDCl$_3$, 300 MHz) $\delta_H$ 4.52 (2H, t, J=5.8 Hz), 3.36 (2H, t, J=7.2 Hz), 3.34 (2H, t, J=5.8 Hz), 3.03 (2H, t, J=7.2 Hz), 2.25 (3H, s), 2.11 (3H, s); $^{13}$C NMR (CDCl$_3$, 75 MHz) $\delta_C$ 204.0 (qC), 170.2 (qC), 57.5 (CH$_2$), 52.8 (CH$_2$), 48.5 (CH$_2$), 34.9 (CH$_2$), 29.8 (CH$_3$), 20.7 (CH$_3$); ESIMS m/z 245 [M+Na]$^+$; HRESIMS m/z 245.0458 [M+Na]$^+$ (calcd for C$_8$H$_{14}$O$_5$SNa, 245.0460).

Preparation 5

To a stirring solution of the compound represented by formula 3 (20.0 mg, 0.114 mmole) and triethylamine (25 µL)

in dichloromethane (2 mL) was slowly added benzoyl chloride (50 μL) at room temperature. The reaction was continued for 5 hours and the solvent-free product was subjected to silica gel column chromatography (eluted with hexane/EtOAc=5:3) for obtaining a compound represented by formula 5 (29.8 mg, yield 92%).

Compound represented by formula 5: colorless crystals, mp=79-80° C.; IR (KBr) $v_{max}$ 1714, 1710, 1315, 1276, 1133, 1119 cm$^{-1}$; $^1$H NMR (CDCl$_3$, 300 MHz) $\delta_H$ 8.04 (2H, d, J=7.5 Hz), 7.60 (1H, t, J=7.5 Hz), 7.47 (2H, t, J=7.5 Hz), 4.78 (2H, t, J=5.7 Hz), 3.48 (2H, t, J=5.7 Hz), 3.41 (2H, t, J=7.2 Hz), 3.03 (2H, t, J=7.2 Hz), 2.21 (3H, s); $^{13}$C NMR (CDCl$_3$, 75 MHz) $\delta_C$ 203.8 (qC), 165.8 (qC), 133.5 (CH), 129.6 (CH×2), 129.0 (qC), 128.6 (CH×2), 58.0 (CH$_2$), 53.0 (CH$_2$), 48.6 (CH$_2$), 34.9 (CH$_2$), 29.7 (CH$_3$); ESIMS m/z 307 [M+Na]$^+$; HRESIMS m/z 307.0613 [M+Na]$^+$ (calcd for C$_{13}$H$_{16}$O$_5$SNa, 307.0616).

Preparation 6

Similar to Preparation 1, α,β-unsaturated carbonyl compounds including ethyl vinyl ketone, ethyl acrylate, N,N-dimethylacrylamide, 4-acryloylmorpholine, and acrylamide were independently reacted with 2-mercaptoethanol to give the corresponding thioether compounds represented by formulas 6 (yield 100%), 8 (yield 100%), 10 (yield 100%), 12 (yield 100%), and 14 (yield 90%), respectively. The above reactions were carried out in the presence of acetone, except for that of preparing the compound represented by formula 14 required the presence of a more polar solvent (methanol/acetone=1:1), due to the unsatisfactory solubility of acrylamide. The intermediates with formulas 6, 8, 10, 12, and 14 were oxidized with hydrogen peroxide, similar to Preparation 2 for obtaining compounds represented by formula 7 (yield 87%), 9 (yield 85%), 11 (yield 87%), 13 (yield 83%), and 15 (yield 84%), respectively. Furthermore, the reaction of ethyl acrylate and 2-mercaptoethanol, proceeded without the presence of a solvent, afforded both compounds represented by formula 8 (yield 45%) and formula 16 (yield 22%). Compound represented by formula 17 was prepared by oxidizing the compound represented by formula 16 with hydrogen peroxide (yield 84%).

Compound represented by formula 6: colorless oil; IR (KBr) $v_{max}$ 3418, 1714, 1458, 1411, 1375, 1361, 1113, 1046, 1013 cm$^{-1}$; $^1$H NMR (CDCl$_3$, 300 MHz) $\delta_H$ 3.75 (2H, t, J=6.2 Hz), 2.70-2.80 (6H, m), 2.48 (2H, q, J=7.3 Hz), 1.06 (3H, t, J=7.3 Hz); $^{13}$C NMR (CDCl$_3$, 75 MHz) $\delta_C$ 209.9 (qC), 60.6 (CH$_2$), 42.0 (CH$_2$), 35.9 (CH$_2$), 34.8 (CH$_2$), 25.3 (CH$_2$), 7.3 (CH$_3$); ESIMS m/z 185 [M+Na]$^+$; HRESIMS m/z 185.0611 [M+Na]$^+$ (calcd for C$_7$H$_{14}$O$_2$SNa, 185.0612).

Compound represented by formula 7: colorless oil; mp=44-45° C.; IR (KBr) $v_{max}$ 3419, 1715, 1312, 1280, 1123 cm$^{-1}$; $^1$H NMR (CDCl$_3$, 300 MHz) $\delta_H$ 4.01 (2H, t, J=5.2 Hz), 3.36 (2H, t, J=7.3 Hz), 3.19 (2H, t, J=5.2 Hz), 2.93 (2H, t, J=7.3 Hz), 2.47 (2H, q, J=7.3 Hz), 1.01 (3H, t, J=7.3 Hz); $^{13}$C NMR (CDCl$_3$, 75 MHz) $\delta_C$ 207.6 (qC), 56.0 (CH$_2$), 55.7 (CH$_2$), 48.8 (CH$_2$), 35.8 (CH$_2$), 33.6 (CH$_2$), 7.5 (CH$_3$); ESIMS m/z 217 [M+Na]$^+$; HRESIMS m/z 217.0508 [M+Na]$^+$ (calcd for C$_7$H$_{14}$O$_4$SNa, 217.0510).

Compound represented by formula 8: colorless oil; IR (KBr) $v_{max}$ 3440, 1732, 1373, 1249, 1185, 1044 cm$^{-1}$; $^1$H NMR (CDCl$_3$, 300 MHz) $\delta_H$ 4.16 (2H, q, J=7.1 Hz), 3.74 (2H, t, J=6.1 Hz), 2.82 (2H, t, J=7.1 Hz), 2.74 (2H, t, J=6.1 Hz), 2.62 (2H, t, J=7.1 Hz), 1.27 (3H, t, J=7.1 Hz); $^{13}$C NMR (CDCl$_3$, 75 MHz) $\delta_C$ 172.1 (qC), 60.8 (CH$_2$×2), 35.1 (CH$_2$), 34.9 (CH$_2$), 26.8 (CH$_2$), 14.2 (CH$_3$); ESIMS m/z 201 [M+Na]$^+$; HRESIMS m/z 201.0563 [M+Na]$^+$ (calcd for C$_7$H$_{14}$O$_3$SNa, 201.0561).

Compound represented by formula 9: colorless oil; IR (KBr) $v_{max}$ 3503, 1732, 1313, 1281, 1120, 1065 cm$^{-1}$; $^1$H NMR (CDCl$_3$, 300 MHz) $\delta_H$ 4.19 (2H, q, J=7.1 Hz), 4.12 (2H, t, J=5.0 Hz), 3.46 (2H, t, J=7.4 Hz), 3.25 (2H, t, J=5.0 Hz), 2.88 (2H, t, J=7.4 Hz), 1.28 (3H, t, J=7.1 Hz); $^{13}$C NMR (CDCl$_3$, 75 MHz) $\delta_C$ 170.7 (qC), 61.5 (CH$_2$), 56.2 (CH$_2$), 55.6 (CH$_2$), 49.9 (CH$_2$), 26.8 (CH$_2$), 14.0 (CH$_3$); ESIMS m/z 233 [M+Na]$^+$; HRESIMS m/z 233.0458 [M+Na]$^+$ (calcd for C$_7$H$_{14}$O$_5$SNa, 233.0460).

Compound represented by formula 10: colorless oil; IR (KBr) $v_{max}$ 3399, 1630, 1500, 1403, 1143, 1048, 1014 cm$^{-1}$; $^1$H NMR (CDCl$_3$, 300 MHz) $\delta_H$ 3.77 (2H, t, J=5.9 Hz), 3.02 (3H, s), 2.96 (3H, s), 2.87 (2H, t, J=7.2 Hz), 2.75 (2H, t, J=5.9 Hz), 2.62 (2H, t, J=7.2 Hz); $^{13}$C NMR (CDCl$_3$, 75 MHz) $\delta_C$ 171.1 (qC), 60.8 (CH$_2$), 37.0 (CH$_3$), 35.4 (CH$_3$×1, CH$_2$×1), 33.5 (CH$_2$), 26.8 (CH$_2$); ESIMS m/z 200 [M+Na]$^+$; HRESIMS m/z 200.0719 [M+Na]$^+$ (calcd for C$_7$H$_{15}$NO$_2$SNa, 200.0721).

Compound represented by formula 11: colorless oil; IR (KBr) $v_{max}$ 3371, 1634, 1503, 1405, 1312, 1278, 1119, 1065 cm$^{-1}$; $^1$H NMR (CDCl$_3$, 300 MHz) $\delta_H$ 4.06 (2H, t, J=5.2 Hz), 3.49 (2H, t, J=7.2 Hz), 3.25 (2H, t, J=5.2 Hz), 3.03 (3H, s), 2.94 (3H, s), 2.87 (2H, t, J=7.2 Hz); $^{13}$C NMR (CDCl$_3$, 75 MHz) $\delta_C$ 169.4 (qC), 56.2 (CH$_2$), 56.0 (CH$_2$), 50.3 (CH$_2$), 37.1 (CH$_3$), 35.7 (CH$_3$), 25.7 (CH$_2$); ESIMS m/z 232 [M+Na]$^+$; HRESIMS m/z 232.0618 [M+Na]$^+$ (calcd for C$_7$H$_{15}$NO$_4$SNa, 232.0619).

Compound represented by formula 12: colorless oil; IR (KBr) $v_{max}$ 3418, 1633, 1463, 1437, 1271, 1248, 1115, 1067, 1028 cm$^{-1}$; $^1$H NMR (CDCl$_3$, 300 MHz) $\delta_H$ 3.76 (2H, t, J=6.0 Hz), 3.69 (4H, m), 3.63 (2H, m), 3.48 (2H, dd, J=4.5, 4.9 Hz), 2.87 (2H, t, J=7.2 Hz), 2.74 (2H, t, J=6.0 Hz), 2.63 (2H, t, J=7.2 Hz); $^{13}$C NMR (CDCl$_3$, 75 MHz) $\delta_C$ 169.8 (qC), 66.6 (CH$_2$), 66.3 (CH$_2$), 60.8 (CH$_2$), 45.7 (CH$_2$), 41.9 (CH$_2$), 35.2 (CH$_2$), 33.2 (CH$_2$) 26.8 (CH$_2$); ESIMS m/z 242 [M+Na]$^+$; HRESIMS m/z 242.0815 [M+Na]$^+$ (calcd for C$_9$H$_{17}$NO$_3$SNa, 242.0813).

Compound represented by formula 13: colorless needles; mp=109-110° C.; IR (KBr) $v_{max}$ 3420, 1637, 1452, 1311, 1275, 1117, 1067, 1028 cm$^{-1}$; $^1$H NMR (CDCl$_3$, 300 MHz) $\delta_H$ 4.06 (2H, t, J=5.2 Hz), 3.57-3.67 (6H, m), 3.49 (2H, t, J=7.2 Hz), 3.47 (2H, m), 3.25 (2H, t, J=5.2 Hz), 2.86 (2H, t, J=7.2 Hz); $^{13}$C NMR (CDCl$_3$, 75 MHz) $\delta_C$ 168.0 (qC), 66.5 (CH$_2$), 66.3 (CH$_2$), 56.2 (CH$_2$), 56.0 (CH$_2$), 50.2 (CH$_2$), 45.7 (CH$_2$), 42.3 (CH$_2$), 25.3 (CH$_2$); ESIMS m/z 274 [M+Na]$^+$; HRESIMS m/z 274.0722 [M+Na]$^+$ (calcd for C$_9$H$_{17}$NO$_5$SNa, 274.0725).

Compound represented by formula 14: white powder; IR (KBr) $v_{max}$ 3354, 3196, 1661, 1414 cm$^{-1}$; $^1$H NMR (pyridine-d5, 300 MHz) $\delta_H$ 4.02 (2H, t, J=6.7 Hz), 3.13 (2H, t, J=7.2 Hz), 2.93 (2H, t, J=6.7 Hz), 2.82 (2H, t, J=7.2 Hz); $^{13}$C NMR (pyridine-d5, 75 MHz) $\delta_C$ 174.3 (qC), 61.7 (CH$_2$), 36.6 (CH$_2$), 35.2 (CH$_2$), 28.1 (CH$_2$); ESIMS m/z 172 [M+Na]$^+$; HRESIMS m/z 172.0407 [M+Na]$^+$ (calcd for C$_5$H$_{11}$NO$_2$SNa, 172.0408).

Compound represented by formula 15: white powder; IR (KBr) $v_{max}$ 3370, 3200, 1661, 1395 cm$^{-1}$; $^1$H NMR (pyridine-d5, 300 MHz) $\delta_H$ 4.35 (2H, t, J=5.6 Hz), 4.06 (2H, t, J=7.6 Hz), 3.64 (2H, t, J=5.6 Hz), 3.25 (2H, t, J=7.6 Hz); $^{13}$C NMR (pyridine-d5, 75 MHz) $\delta_C$ 174.3 (qC), 61.7 (CH$_2$), 36.6 (CH$_2$), 35.2 (CH$_2$), 28.1 (CH$_2$); ESIMS m/z 204 [M+Na]$^+$; HRESIMS m/z 204.0305 [M+Na]$^+$ (calcd for C$_5$H$_{11}$NO$_4$SNa, 204.0306).

Compound represented by formula 16: colorless oil; IR (KBr) $v_{max}$ 3438, 1731, 1377, 1299, 1206, 1162, 1043 cm$^{-1}$; $^1$H NMR (CDCl$_3$, 300 MHz) $\delta_H$ 4.10 (2H, q, J=7.0 Hz), 4.05 (2H, q, J=7.0 Hz), 3.65 (2H, t, J=6.0 Hz), 2.54-2.74 (5H, m), 2.28 (2H, m), 1.91 (2H, m), 1.20 (3H, t, J=7.0 Hz), 1.18 (3H, t, J=7.0 Hz); $^{13}$C NMR (CDCl$_3$, 75 MHz) $\delta_C$ 174.1 (qC), 172.8 (qC), 60.89 (CH$_2$), 60.86 (CH$_2$), 60.6 (CH$_2$), 45.3 (CH), 35.5 (CH$_2$), 33.6 (CH$_2$), 31.7 (CH$_2$) 26.7 (CH$_2$), 14.22 (CH$_3$), 14.18 (CH$_3$); ESIMS m/z 301 [M+Na]$^+$; HRESIMS m/z 301.1084 [M+Na]$^+$ (calcd for C$_{12}$H$_{22}$O$_5$SNa, 301.1086).

Compound represented by formula 17: colorless oil; IR (KBr) $\nu_{max}$ 3439, 1732, 1380, 1312, 1290, 1206, 1120 cm$^{-1}$; $^1$H NMR (CDCl$_3$, 300 MHz) $\delta_H$ 4.21 (2H, q, J=7.1 Hz), 4.15 (2H, q, J=7.1 Hz), 4.11 (2H, t, J=5.3 Hz), 3.72 (1H, dd, J=14.2, 9.3 Hz), 3.25 (2H, t, J=5.3 Hz), 3.21 (1H, dd, J=14.2, 4.9 Hz), 3.13 (1H, m), 2.39 (2H, t, J=7.4 Hz), 2.04 (2H, t, J=7.4 Hz), 1.30 (3H, t, J=7.1 Hz), 1.27 (3H, t, J=7.1 Hz); $^{13}$C NMR (CDCl$_3$, 75 MHz) $\delta_C$ 173.0 (qC), 172.4 (qC), 61.6 (CH$_2$), 60.8 (CH$_2$), 56.4 (CH$_2$), 55.1 (CH$_2$), 55.8 (CH$_2$), 38.7 (CH), 31.1 (CH$_2$) 27.2 (CH$_2$), 14.1 (CH$_3$), 14.0 (CH$_3$); ESIMS m/z 333 [M+Na]$^+$; HRESIMS m/z 333.0986 [M+Na]$^+$ (calcd for C$_{12}$H$_{22}$O$_7$SNa, 333.0987).

Experimental Section

Materials

Dihydroaustrasulfone alcohol is the synthetic precursor of austrasulfone, which is a marine natural product possessing neuroprotective activity. Dihydroaustrasulfone alcohol was prepared by the reaction of 2-mercaptoethanol with methyl vinyl ketone to produce the corresponding sulfide, followed by oxidation of this sulfide with m-chloroperoxybenzoic acid.

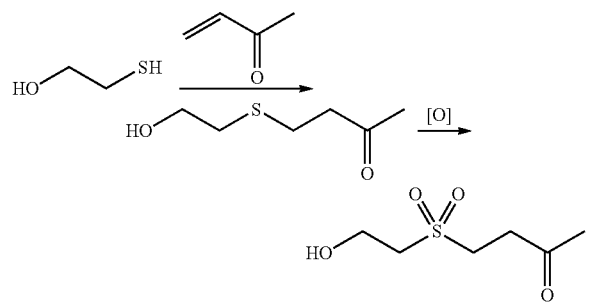

3-(4,5-Dimetylthiazol-2-yl)-2,5-diphenyltetrazolium bromide (MTT), RNase A, propidium iodide (PI), trypsin, BSA, Tween-20, -80 and DMSO were purchased from Amresco Inc. (Solon, Ohio, USA). F-12 and fetal bovine serum (FBS) were purchased from GIBCO BRL (Rockville, Md., USA). Cell culture supplies were purchased from Costar (Corning, Inc., Cypress, Calif., USA). The antibodies against AKT, Rac-1, MAPK/extracellular signal-regulated kinase (ERK) 1/2, c-Jun NH2-terminal kinase (JNK)/stress-activated protein kinase, and p38 MAPK proteins and phosphorylated proteins were purchased from Cell Signaling Technology (Beverly, Mass., USA). Anti-ERK1/2, anti-PI3K, antifocal adhesion kinase (FAK), anti-p-FAK, and horseradish peroxidase-conjugated goat antimouse IgG antibodies were purchased from Santa Cruz Biotechnology Co. (Santa Cruz, Calif., USA). β-actin was purchased from Chemicon (Temecula, Calif., USA).

Cell Lines and Cultures

Human NSCLC A549 cells were obtained from Food Industry Research and Development Institute (Hsinchu, Taiwan). A549 cells were cultured in F-12 medium (Gibco BRL, Rockville, Md., USA) containing 10% fetal bovine serum (FBS) (Gibco BRL, Rockville, Md., USA), 100 U/mL penicillin, and 100 mg/mL streptomycin (Gibco BRL, Rockville, Md., USA) at 37° C. in a humidified atmosphere comprised of 95% air and 5% CO$_2$. In all of the experiments, the medium was supplemented with 1% (v/v) fetal bovine serum (FBS). LLC cells were obtained from the American Type Culture Collection (ATCC; CRL-1642) and maintained as monolayer cultures in DMEM supplemented with 10% (v/v) FBS, 1% non-essential amino acids and 1% sodium pyruvate. All cells were incubated in a humidifier with 5% CO$_2$ at 37° C.

Cell Proliferation Assay

The MTT assay was performed in the A549 cell lines to measure the cytotoxicity of dihydroaustrasulfone alcohol. All cell lines were seeded in 96-well plates with 2×10$^4$ cells/well in culture medium. Dihydroaustrasulfone alcohol was dissolved in PBS. The cells were treated with various concentrations of dihydroaustrasulfone alcohol as indicated in each figure. After 24 h, the number of viable cells was determined. Then, 5 mg/mL MTT was added to each well, and the plate was incubated at 37° C. for 3 h. The medium was removed, and 50 µL DMSO was added. The absorbance at 590 nm was measured for each well on an ELISA reader. The data are presented as the mean±SEM of three independent experiments.

Flow Cytometry Analysis

A549 cells (2×10$^5$) were seeded into each well of a 12-well plate (TPP; Techno Plastic Products AG, Trasadingen, Switzerland) 24 h before being treated with various concentrations of dihydroaustrasulfone alcohol for 24 h. The cells were harvested with trypsin-EDTA, washed twice with 10 mL ice-cold PBS, fixed in 70% (v/v) ethanol, and kept at 4° C. The cells were then stained with propidium iodide (PI) [100 µg/mL PI, 0.2% (v/v) Nonidet P-40, and 1 mg/mL RNase A (DNase-free) in PBS lacking Ca$^{2+}$ and Mg$^{2+}$ at a 1:1:1 ratio by volume] and the DNA contents were analyzed with flow cytometry (Becton Dickinson, San Jose, Calif., USA). The intensity of PI fluorescence was linearly amplified, and both the area and width of the fluorescence pulse were measured. Ten thousand events were acquired, and the percentage of hypodiploid (apoptosis, sub-G1) events and the percentages of cells in the G0/G1, S and G2/M phases were determined using the DNA analysis software ModFitL T, version 2.0 (Verity Software, Topsham, Me., USA).

Wound Healing Assay

For cell motility determination, A549 cells (2×10$^5$ cells/mL) were seeded in a 12-well tissue culture plate. After one day, the center of the cell monolayers was scraped with a sterile micropipette tip to create a straight zone (gap) of constant width. Then, each well was washed with PBS, and A549 cells were exposed to various concentrations of dihydroaustrasulfone alcohol (20, 30 or 40 µg/mL). Wound closure was monitored and photographed at 0 h and 18 h with a Nikon inverted microscope. To quantify the migrated cells, pictures of the initial wounded monolayers were compared with the corresponding pictures of cells at the end of the incubation. Artificial lines fitting the cutting edges were drawn on pictures of the original wounds and overlaid on the pictures of cultures after incubation. Cells that had migrated across the white lines were counted in six random fields from each triplicate treatment.

Cell Migration Assay

Tumor cell migration was assayed in trans-well chambers (Millipore) according to the method reported by Huang et al. (Lai, K. C.; Huang, A. C.; Hsu, S. C.; Kuo, C. L.; Yang, J. S.; Wu, S. H.; Chung, J. G. Benzyl isothiocyanate (BITC) inhibits migration and invasion of human colon cancer HT29 cells by inhibiting matrix metalloproteinase-2/-9 and urokinase plasminogen (uPA) through PKC and MAPK signaling pathway. *J. Agric. Food Chem.* 2010, 58, 2935-2942), with some modifications. Briefly, trans-well chambers with 6.5 mm polycarbonate filters of 8 μM pore size were used. A549 cells (1×10⁴ cells/mL) and 20, 30 or 40 μg/mL of dihydroaustrasulfone alcohol were suspended in F-12 (100 μL, serum free), placed in the upper trans-well chamber, and incubated for 24 h at 37° C. Then, the cells on the upper surface of the filter were completely wiped away with a cotton swab, and the lower surface of the filter was fixed in methanol, stained with 10% Giemsa solution, and counted under a microscope at a magnification of 200×. For each replicate, the tumor cells in 10 randomly selected fields were determined and the counts were averaged.

Determination of MMP-2 and MMP-9 by Zymography

MMPs in the medium released from A549 cells were assayed using gelatin zymography (8% zymogram gelatin gels) according to the methods reported by Huang et al., with some modification (Lai, K. C.; Huang, A. C.; Hsu, S. C.; Kuo, C. L.; Yang, J. S.; Wu, S. H.; Chung, J. G. Benzyl isothiocyanate (BITC) inhibits migration and invasion of human colon cancer HT29 cells by inhibiting matrix metalloproteinase-2/-9 and urokinase plasminogen (uPA) through PKC and MAPK signaling pathway. *J. Agric. Food Chem.* 2010, 58, 2935-2942) (Chen, Y. Y.; Chou, P. Y.; Chien, Y. C.; Wu, C. H.; Wu, T. S.; Sheu, M. J. Ethanol extracts of fruiting bodies of *Antrodia cinnamomea* exhibit anti-migration action in human adenocarcinoma CL1-0 cells through the MAPK and PI3K/AKT signaling pathways. *Phytomedicine* 2012, 19, 768-778). Briefly, the culture medium was electrophoresed (80 V for 120 min) in an 8% SDS-PAGE gel containing 0.1% gelatin. The gel was then washed at room temperature in a solution containing 2.5% (v/v) Triton X-100 with two changes and subsequently transferred to a reaction buffer for enzymatic reaction containing 1% $NaN_3$; 10 mM $CaCl_2$; and 40 mM Tris-HCl, pH 8.0; at 37° C. with shaking overnight (for 12-15 h). Finally, the MMP gel was stained for 30 mM with 0.25% (w/v) Coomassie blue in 10% acetic acid (v/v) and 20% methanol (v/v) and destained in 10% acetic acid (v/v) and 20% methanol (v/v).

Western Blotting Analysis

A549 cells were plated in 10-cm dishes at a density of 3×10⁶ cells per dish and incubated with 20, 30 or 40 μg/mL dihydroaustrasulfone alcohol in F-12 containing 1% (v/v) FBS for 24 h. The cells were collected, lysed in a lysis solution, and then incubated at 25° C. for 10 min. Total proteins were separated with SDS-PAGE before being transferred to PVDF membranes. The membranes were blocked with 5% (v/v) nonfat dry milk in PBS-Tween 20 for one hour and changed to an appropriate dilution of specific primary antibodies in TBS-T buffer overnight at 4° C. The blots were then incubated with horseradish peroxidase-linked secondary antibody for 1 h and then developed with the electrochemiluminescence (ECL) reagent and exposed to Hyperfilm (Amersham, Arlington Height, Ill., USA). The data were analyzed by Gel-Logic 200 Imaging Systems, Molecular Imaging Software.

Lewis Lung Cancer Cell Bearing Tumor Model of C57BL/6J Mice

The animal experiments were approved by the Institutional Animal Care and Use Committee of China Medical University (approval ID: 102-194-C). All animal care followed the institutional animal ethical guidelines of China Medical University. C57BL/6J male mice (average 25-28 g; 6 weeks old) were obtained from the Laboratory Animal Center, College of Medicine, National Taiwan University (Taipei, Taiwan). The C57BL/6J mice were kept on a 12 h light/dark cycle at 25° C. C57BL/6J mice were subcutaneously implanted with LLC cells (7×10⁵ cells in 100 μL). The treatment of dihydroaustrasulfone alcohol start while all the tumors volume were larger than 100 mm³. Eighteen mice were randomly assigned to three treatment groups (6 animals per group). Group I (untreated group) was subcutaneously grafted with LLC cells and given vehicle solvent. Group II was grafted with LLC cells and then treated with dihydroaustrasulfone alcohol (8 mg/kg). Group III was grafted with LLC cells and then treated with dihydroaustrasulfone alcohol (16 mg/kg). The dihydroaustrasulfone alcohol was diluted in normal saline and administered by IP. Body weight and tumor volume were measured every week after cell injection. The tumor width (W) and length (L) were measured every week by calipers, and the tumor volume was calculated as L×W2×0.52. The mice were treated daily for 2 weeks and then sacrificed.

Statistical Analysis

The values are presented as the mean±SD relative to the control values. Statistically significant differences from the control group were identified by one-way ANOVA for the data. P<0.05 was considered statistically significant for all tests.

Results

Figure 1B:
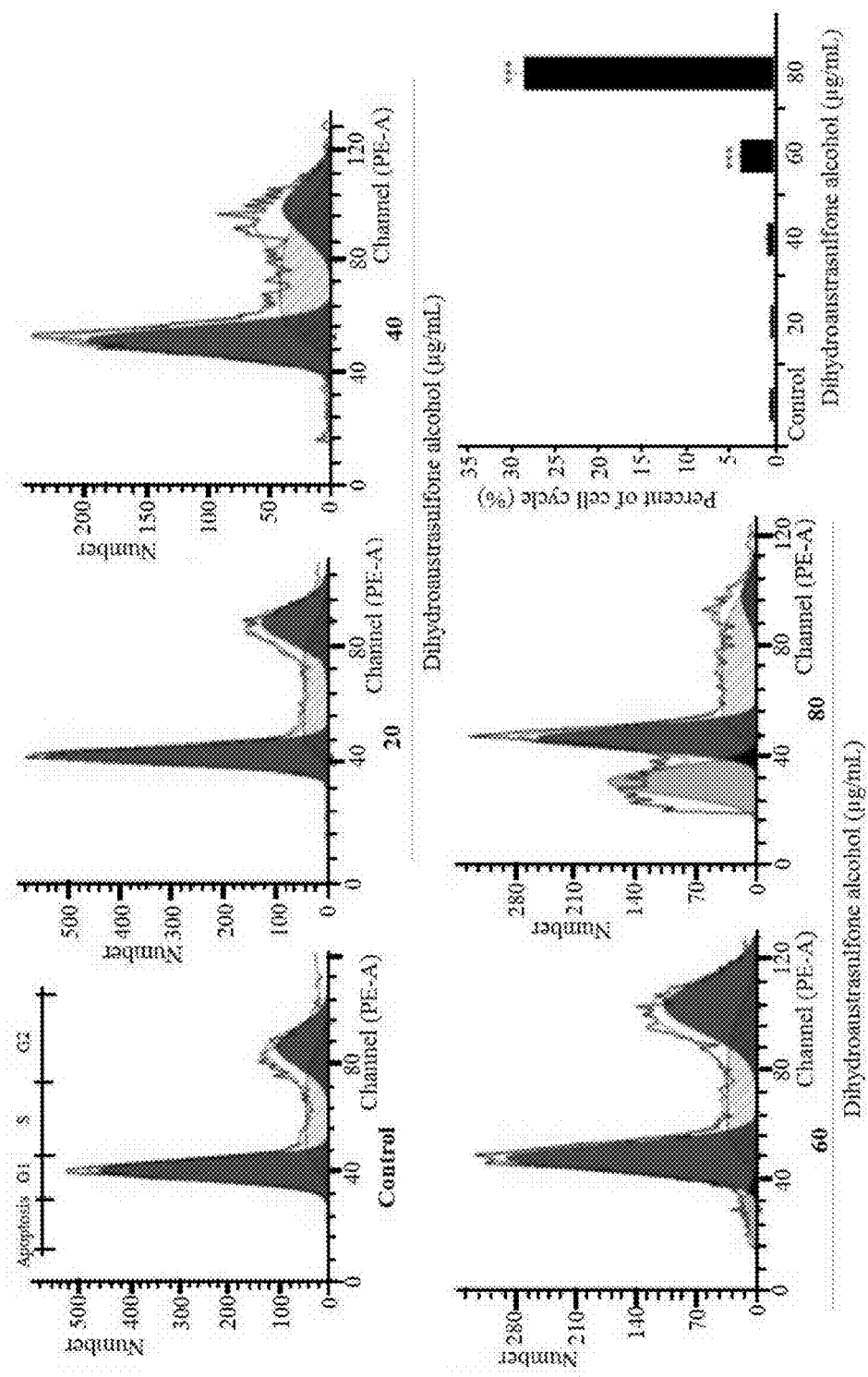

Cytotoxicity of Dihydroaustrasulfone Alcohol in A549 Cells 3-(4,5-Dimethylthiazol-2-yl)-2,5-diphenyltetrazolium bromide (MTT) assay is broadly used to test cell cytotoxicity. To determine whether dihydroaustrasulfone alcohol decreases cancer cell viability, A549 cells were screened using the MTT assay for cell cytotoxicity in the presence of different concentrations of dihydroaustrasulfone alcohol for 24 h. As shown in FIG. 1a, dihydroaustrasulfone alcohol significantly inhibited the viability of A549 cells in a concentration-dependent manner ($IC_{50}$=0.273 mM). Because the MTT assay showed that dihydroaustrasulfone alcohol at 60, 80, and 100 μg/mL significantly suppressed cell viability, we postulated that the inhibitory effects of dihydroaustrasulfone alcohol on cell viability might be mediated by apoptosis. Therefore, the effect of dihydroaustrasulfone alcohol concentration on the cell cycle and apoptosis was evaluated at 20, 40, 60, or 80 μg/mL (FIG. 1b). The results demonstrated that treatment for 24 h with dihydroaustrasulfone alcohol at 20 and 40 μg/mL had no effect on apoptosis in the sub-G1 phase (FIG. 1b). Therefore, the concentrations 20, 30, and 40 μg/mL were selected for subsequent studies.

Effect of Dihydroaustrasulfone Alcohol on a Wound-Healing Assay in A549 Cells

Figure 2A:
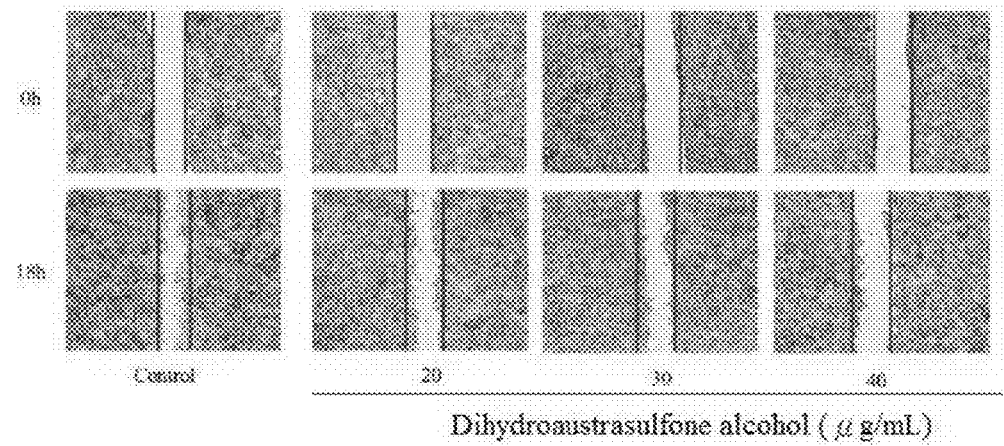
FIG. 2. Effects of dihydroaustrasulfone alcohol on the wound healing migration of A549 cells. (a) A wound was introduced by scraping confluent cell layers with a pipet tip. A549 cells were incubated with dihydroaustrasulfone alcohol (20, 30, or 40 μg/mL) for 18 h, and the migration distances of the cells were calculated. Representative photographs of invading cells that received either control or dihydroaustrasulfone alcohol treatment. (b) Cell that migrated across the red lines were counted in six random fields in each treatment. The mean number of cells in the denuded zone was in three independent experiments. The values (means±SD, n=3) differed significantly (*P<0.05; **P<0.01).
Figure 2B:
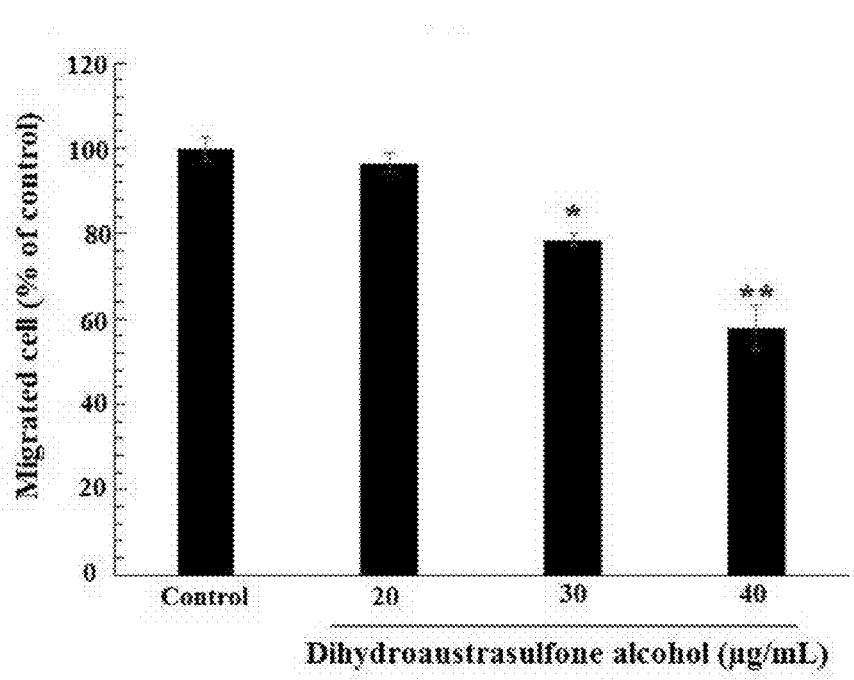

Wound healing assay were broadly used in research focused on cancer cell migratory ability inhibition. To evaluate the effect of dihydroaustrasulfone alcohol on the migration of lung cancer cells, we used a trans-well assay and a wound healing assay. For the latter, the confluent monolayer was scraped with a sterile micropipette tip to create a scratch wound. We found that dihydroaustrasulfone alcohol added at 30 and 40 μg/mL significantly decreased the migration of A549 cells (FIG. 2).

Effect of Dihydroaustrasulfone Alcohol in a Trans-Well Assay with A549 Cells

Figure 3A:
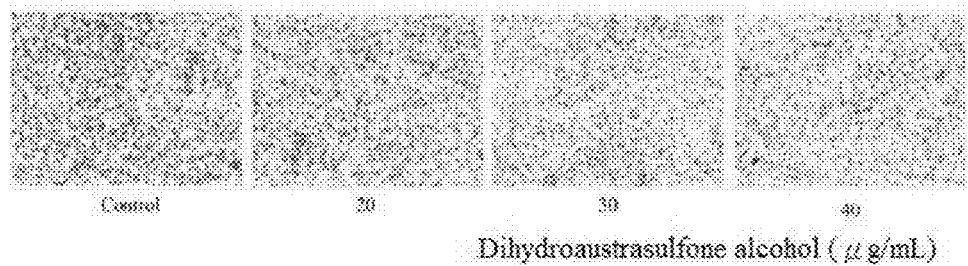
FIG. 3. Effects of dihydroaustrasulfone alcohol on the trans-well migration assay of A549 cells. (a) A549 cells were incubated with dihydroaustrasulfone alcohol (20, 30 or 40 μg/mL) for 18 h, and the (b) trans-well migration of cells was calculated. Photos of the migration of A549 cells were taken under a microscope (200-fold magnification). The values (means±SD, n=3) differed significantly (*P<0.05; **P<0.01).
Figure 3B:
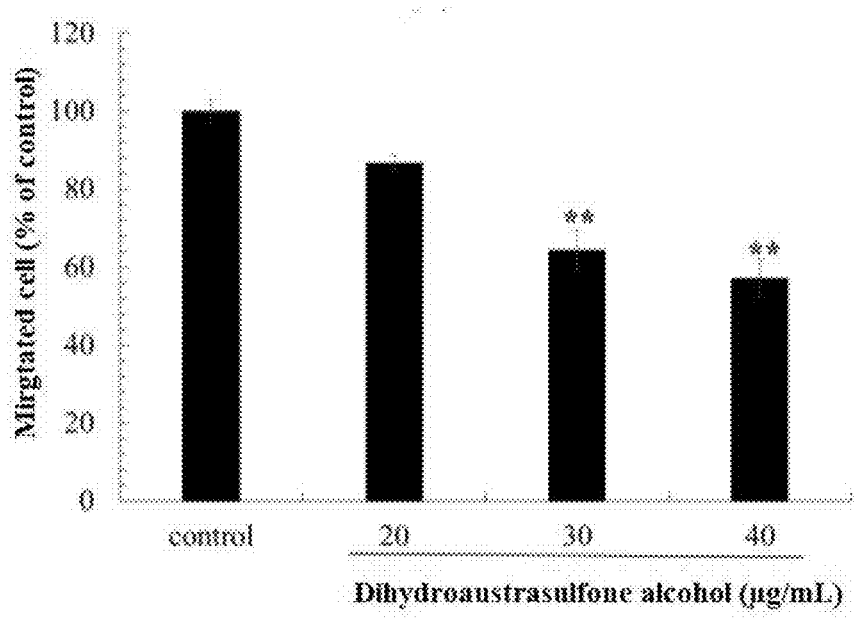

Cancer cell migration inhibition was also commonly studied through trans-well assay. The trans-well assay was also used to investigate the migration of A549 cells after dihydroaustrasulfone alcohol treatment. The results showed that treatment with 30 or 40 μg/mL dihydroaustrasulfone alcohol significantly decreased migration (FIG. 3).

Figure 4A:
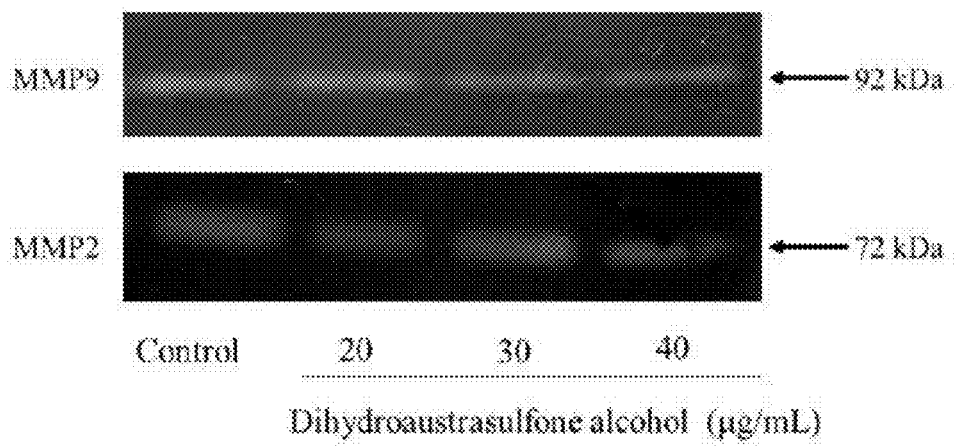
FIG. 4. Effects of dihydroaustrasulfone alcohol on the MMP-2 and MMP-9 activities of A549 cells. (a) The cells were treated with various concentrations (20, 30, or 40 μg/mL) of dihydroaustrasulfone alcohol for 24 h. The conditioned media were collected, and MMP-2 and MMP-9 activities were determined by gelatin zymography. (b) The activities of these proteins were subsequently quantified by densitometric analysis. The values (means±SD, n=3) differed significantly (*P<0.05).
Figure 4B:
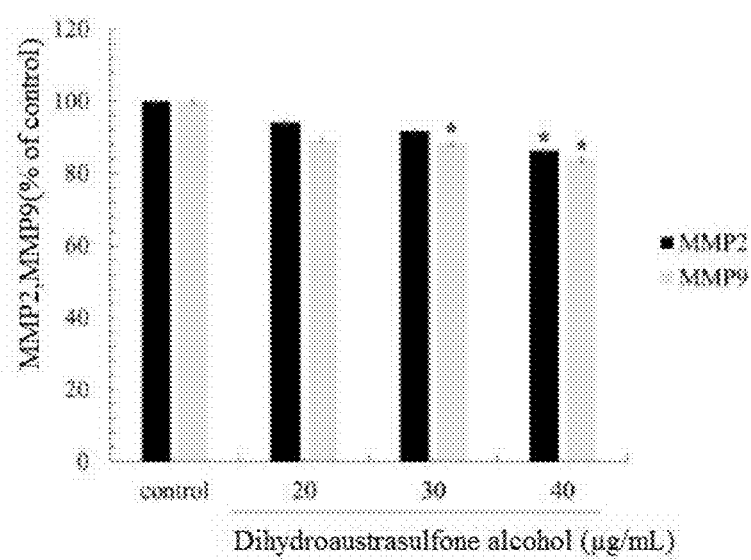

Effect of Dihydroaustrasulfone Alcohol Inhibits the Release of MMP in A549 Cells MMP-2 and MMP-9 were well studied as cancer cell migration and invasion related proteins. Zymography assay is a common method to detect their activities. Through a zymography assay, we found that dihydroaustrasulfone alcohol significantly inhibited the activities of MMP-2 and MMP-9 (FIG. 4). These results demonstrated that the antimetastatic effect of dihydroaustrasulfone alcohol was associated with the inhibition of enzymatically degradative processes of cancer cell migration.

Figure 5:
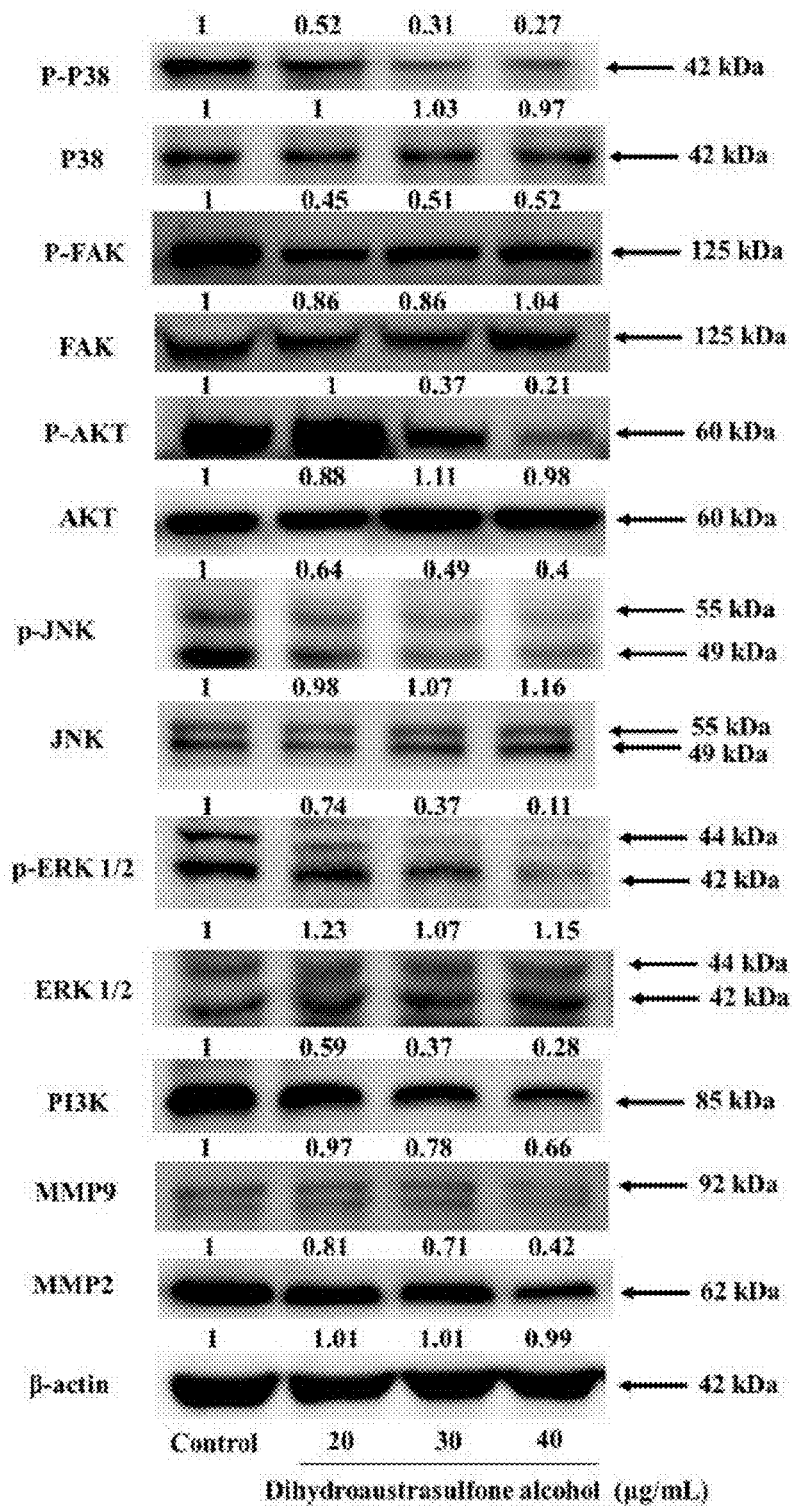
FIG. 5. Effects of dihydroaustrasulfone alcohol on migration-related proteins and PI3K/AKT signaling in A549 cells. A549 cells were treated with 20, 30, or 40 μg/mL, and cell lysates were subjected to SDS-PAGE and Western blotting before quantification by densitometric analyses (using the control as 100%). The values indicate the density proportion of each protein compared with the control.
Figure 7:
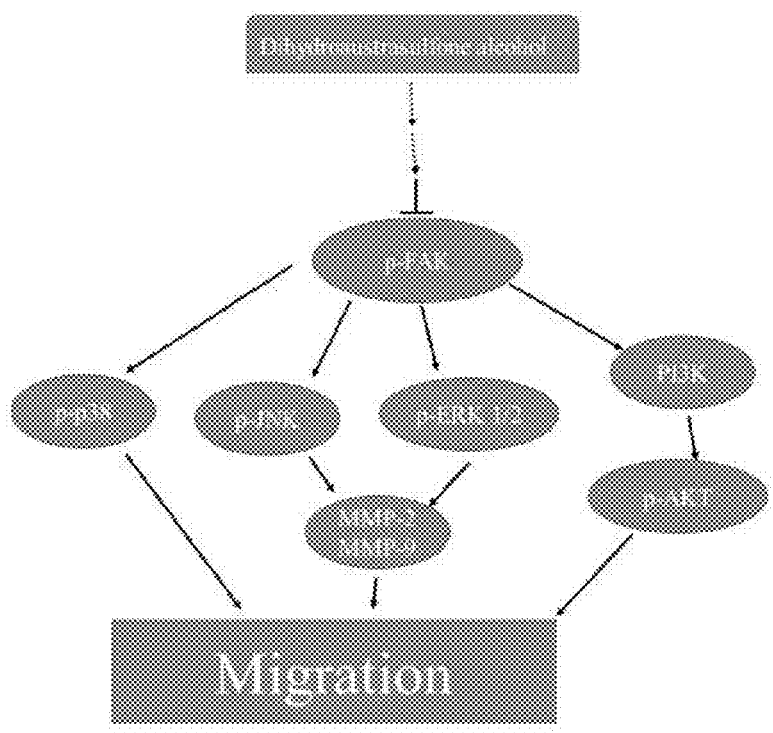
FIG. 7. Proposed signaling pathways for dihydroaustrasulfone alcohol-mediated inhibition of A549 cell migration. The effect of dihydroaustrasulfone alcohol is most likely achieved through the inhibition of FAK, which regulates MMP-2 expression through the MAPK and PI3K/AKT signaling pathways.

Dihydroaustrasulfone Alcohol Inhibits Migration-Related Proteins and PI3K/AKT Signaling in A549 Cells In this invention, we found that dihydroaustrasulfone alcohol inhibited the activation of FAK, as evidenced by reduced phosphorylation of FAK (FIG. 5). We also demonstrated that treatment with dihydroaustrasulfone alcohol inhibited the phosphorylation of ERK1/2 and JNK1/2 (FIG. 5). In addition, we showed that dihydroaustrasulfone alcohol inhibited PI3K/AKT in A549 cells. Thus, it appears that FAK promotes A549 cancer cell migration in concert with the activation of the PI3K/AKT signaling pathways. Increased phosphorylation of FAK and its downstream targets ERK1/2, PI3K, and AKT have been shown in A549 cells stimulated by fibronectin. Several studies have indicated that FAK/PI3K/Akt is involved in the regulation of MMP-2 and MMP-9 activities in different cell types (Campbell, I. G.; Russell, S. E.; Choong, D. Y.; Montgomery, K. G.; Ciavarella, M. L.; Hooi, C. S.; Cristiano, B. E.; Pearson, R. B.; Phillips, W. A. Mutation of the PIK3CA gene in ovarian and breast cancer. *Cancer Res.* 2004, 64, 7678-7681) (Chan, K. C.; Ho, H. H.; Huang, C. N.; Lin, M. C.; Chen, H. M.; Wang, C. J. Mulberry leaf extract inhibits vascular smooth muscle cell migration involving a block of small GTPase and Akt/NF-kappaB signals. *J. Agric. Food Chem.* 2009, 57, 9147-9153). To assess whether dihydroaustrasulfone alcohol inhibits the phosphorylation of FAK, AKT, and the protein level of PI3K, A549 cells were treated with various concentrations of dihydroaustrasulfone alcohol (20, 30, or 40 μg/mL). FIG. 5 shows dihydroaustrasulfone alcohol inhibited the activation of FAK and AKT through a decrease in the phosphorylation of FAK and AKT. In addition, dihydroaustrasulfone alcohol inhibited the protein levels of PI3K in a dose-dependent manner (FIG. 5). Zeng et al. (Zeng, Z. Z.; Jia, Y.; Hahn, N. J.; Markwart, S. M.; Rockwood, K. F.; Livant, D. L. Role of focal adhesion kinase and phosphatidylinositol 3'-kinase in integrin fibronectin receptor-mediated, matrix metalloproteinase-1-dependent invasion by metastatic prostate cancer cells. *Cancer Res.* 2006, 66, 8091-8099) reported that activated FAK-induced PI3K is required for the production of matrix metalloproteinases (MMPs). PI3K is one of the critical downstream signal molecules of FAK pathways (Choi, Y. A.; Lim, H. K.; Kim, J. R.; Lee, C. H.; Kim, Y. J.; Kang, S. S.; Baek, S. H. Group 1B secretory phospholipase A2 promotes matrix metalloproteinase-2-mediated cell migration via the phosphatidylinositol 3-kinase and Akt pathway. *J. Biol. Chem.* 2004, 279, 36579-36585). Therefore, our results demonstrate that dihydroaustrasulfone alcohol inhibited the expressions of p-FAK, pAKT, and PI3K. In addition, Shih et al. (Shih, Y. W.; Chen, P. S.; Wu, C. H.; Jeng, Y. F.; Wang, C. J. Alpha-chaconine-reduced metastasis involves a PI3K/Akt signaling pathway with downregulation of NF-kappaB in human lung adenocarcinoma A549 cells. *J. Agric. Food Chem.* 2007, 55, 11035-11043) reported that the PI3K/AKT signal transduction pathway regulates cell invasion and metastasis of NSCLC and is closely associated with the development and progression of various tumors. Based on our results, the proposed signaling pathways are shown in FIG. 7 for the dihydroaustrasulfone alcohol-induced inhibition of A549 cell migration.

Figure 6A:
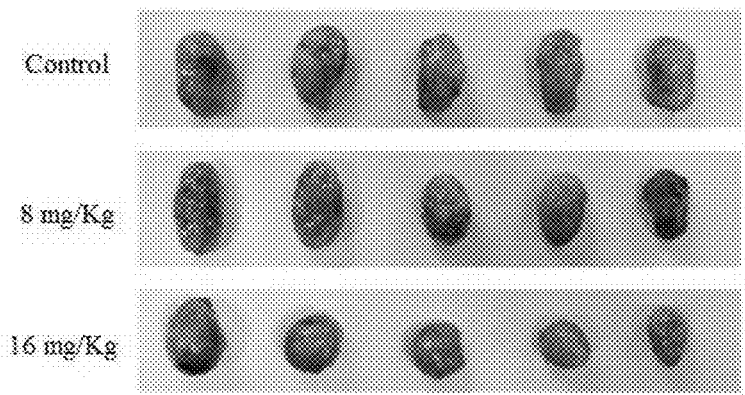
FIG. 6. Antitumor effect of dihydroaustrasulfone alcohol on a Lewis lung carcinoma-bearing tumor model in C57BL/6J mice. Eighteen C57BL/6J mice were randomly divided into 3 groups. (a) Representative subcutaneous tumor mass of mice, (b) solid tumor volume, and (c) body weight from each group are shown. The data are presented as the mean±S.D. of six animals at days 8 and 14 after tumor implantation. ** indicates p<0.01 compared with control group (treated with normal saline) of each group.
Figure 6B:
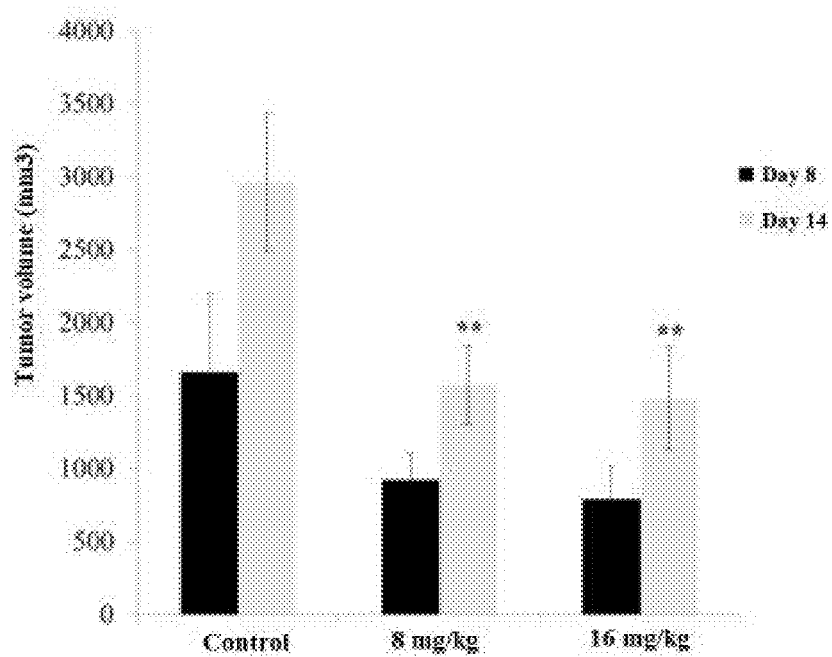
Figure 6C:
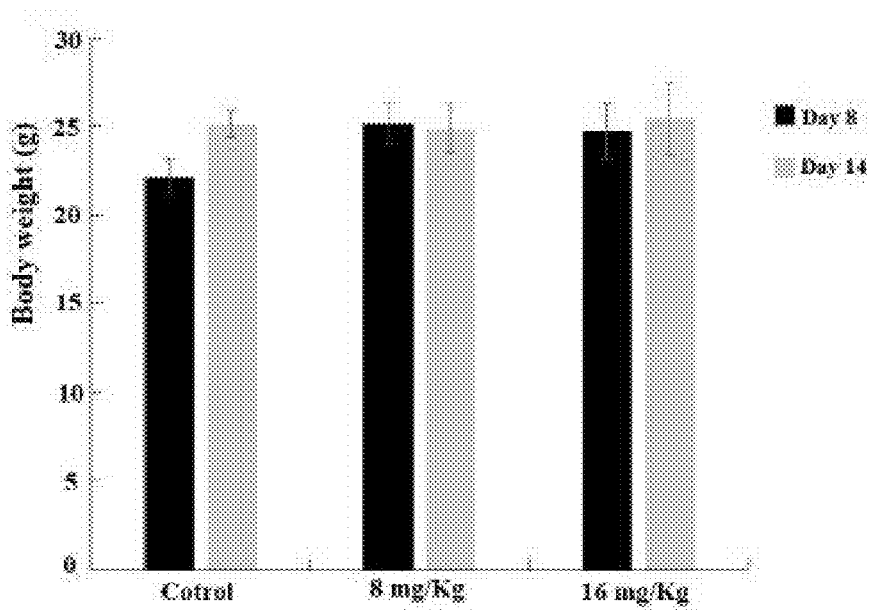

Antitumor Effect of Dihydroaustrasulfone Alcohol on a Lewis Lung Carcinoma (LLC)-Bearing Tumor Model in C57BL/6J Mice In vivo study is necessary to proof anti-tumor growth effect of the test drug. In the invention, we investigated the antitumor effect of dihydroaustrasulfone alcohol in a Lewis lung carcinoma-bearing tumor model in C57BL/6J mice. The results showed that a 14-day treatment of 8 or 16 mg/kg dihydroaustrasulfone alcohol significantly reduced tumor size compared with the LLC control group (FIG. 6). These data also show that the body weights of the mice that received treatment were not significantly different from the LLC control group at days 8 or 14 (FIG. 6c).

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the following claims.

What is claimed is:

1. A method for inhibiting lung cancer metastasis and/or growth comprising administering a subject with a compound represented by the following general formula 1,

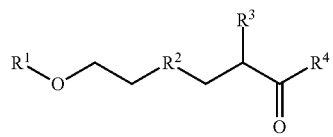

formula 1 wherein:
$R^1$ is selected from the group consisting of H, $R^5$ and $R^5C(=O)$;
$R^2$ is selected from the group consisting of S and $(O=)S(=O)$;
$R^3$ is selected from the group consisting of H, $CH_3$ and $CH_2CH_2C(=O)OR^5$;
$R^4$ is selected from the group consisting of $R^5$, $OR^5$,

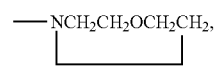

$N(R^5)_2$, $NH_2$, $NHR^5$ and OH; and
$R^5$ is selected from an alkyl group having one to six carbon atoms and an unsubstituted or substituted phenyl group;
provided that when $R^3$ is $CH_2CH_2C(=O)OR^5$, $R^4$ is $OR^5$; and
when $R^1$ is H, $R^2$ is S and $R^3$ is H, $R^4$ is not $CH_3$;
wherein the compound represented by the general formula 1 is selected from the group consisting of formulae 3, 6 to 9, and 18 to 20;

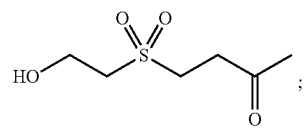

formula 3

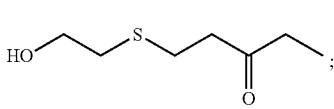

formula 6

-continued
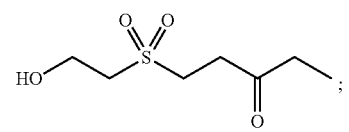
formula 7
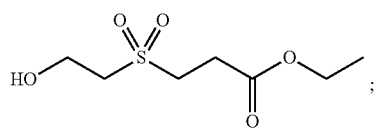
formula 8
formula 9
formula 18
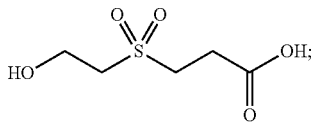
formula 19
and
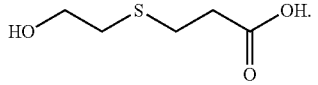
formula 20
2. The method according to claim 1, wherein the lung cancer is non-small cell lung carcinoma.
3. The method according to claim 1, wherein the lung cancer is Lewis lung carcinoma.
4. The method according to claim 1, wherein the compound is administered by injection.
* * * * *